United States Patent [19]

Guerry et al.

[11] Patent Number: 5,137,920

[45] Date of Patent: Aug. 11, 1992

[54] METHOD OF TREATING FUNGAL INFECTIONS

[75] Inventors: Philippe Guerry, Baslé ; Synèse Jolidon, Birsfelden; René Zurflüh, Bülach, all of Switzerland

[73] Assignee: Hoffmann-La Roche Inc., Nutley, N.J.

[21] Appl. No.: 533,605

[22] Filed: Jun. 5, 1990

[30] Foreign Application Priority Data

Jun. 8, 1989 [CH] Switzerland .......................... 2159/89
Mar. 19, 1990 [CH] Switzerland ........................... 890/90

[51] Int. Cl.$^5$ ................. A61K 31/275; A61K 31/135; C07C 255/50; C07C 225/10
[52] U.S. Cl. .................... 514/648; 514/524; 558/415; 564/323
[58] Field of Search ............... 514/648, 524; 564/323; 558/415

[56] References Cited

U.S. PATENT DOCUMENTS

| | | | |
|---|---|---|---|
| 1,894,865 | 1/1933 | Hartmann et al. | |
| 2,668,813 | 2/1954 | Goldberg et al. | |
| 2,668,850 | 2/1954 | Goldberg et al. | |
| 2,796,435 | 6/1957 | Goldberg et al. | |
| 3,123,643 | 3/1964 | Palopoli et al. | 260/570 |
| 3,312,696 | 4/1967 | Turbanti | 260/247.7 |
| 3,553,332 | 1/1971 | Grunberg | 424/330 |
| 3,560,567 | 2/1971 | Ruegg et al. | 260/570 |
| 3,864,501 | 2/1975 | Yokoyama et al. | 426/268 |
| 4,216,326 | 8/1980 | Zenitz | 564/323 X |
| 4,568,695 | 2/1986 | Moran et al. | 514/648 |
| 4,861,916 | 8/1989 | Kohler et al. | 564/323 |

FOREIGN PATENT DOCUMENTS

| | | |
|---|---|---|
| 114410 | 12/1982 | European Pat. Off. . |
| 115080 | 12/1982 | European Pat. Off. . |
| 158237 | 1/1983 | German Democratic Rep. ........................ 564/323 |
| 923727 | 1/1961 | United Kingdom . |

OTHER PUBLICATIONS

Chem. Abst. 52, 440a (1959), Goldberg et al.
Chem. Abst. 63, 6097f (1965), Turbanti et al.

*Primary Examiner*—Joseph Paul Brust
*Attorney, Agent, or Firm*—George M. Gould; George W. Johnston; Alan P. Kass

[57] ABSTRACT

Compunds having the formula

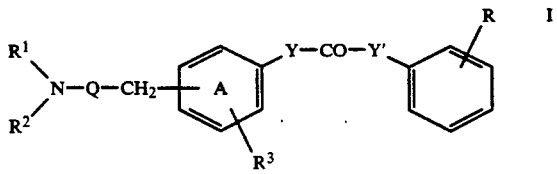

wherein each of $R^1$ and $R^2$ individually is hydrogen, lower alkyl, or lower alkenyl, $R^3$ is hydrogen, halogen or lower alkyl, Q is alkylene with 2 to 11 carbon atoms and at least 2 carbon atoms between the two free valencies or alkenylene with 4 to 11 carbon atoms and at least 4 carbon atoms between the two free valencies and each of Y and Y' individually is a direct bond, the group $R^1R^2$—N—Q—CH$_2$— is attached to the 3- or 4-position of ring A and the symbol R represents that the ring to which it is attached is unsubstituted or is substituted with at least one of halogen, trifluoromethyl, cyano, nitro, lower alkyl or lower alkoxy, and their pharmaceutically acceptable acid addition salts have valuable pharmacological properties. In particular, they have a pronounced antifungal activity and can be used as medicaments, especially for the control or prevention of topical or systemic infections which are caused by pathogenic fungi.

8 Claims, No Drawings

METHOD OF TREATING FUNGAL INFECTIONS

BACKGROUND OF THE INVENTION

Field of the Invention

The invention relates to substituted aminoalkyl benzene derivatives and their pharmaceutically acceptable acid addition salts.

SUMMARY OF THE INVENTION

The present invention describes compounds having the formula:

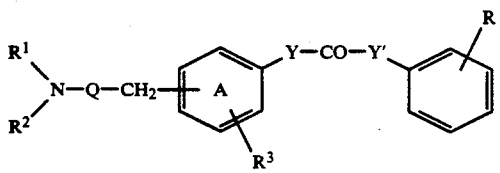

wherein each of $R^1$ and $R^2$ individually is hydrogen, lower alkyl or lower alkenyl or together are straight-chain alkylene with 2 to 4 carbon atoms, $R^3$ is hydrogen, halogen or lower alkyl, Q is alkylene with 2 to 11 carbon atoms and at least 2 carbon atoms between the two free valencies or alkenylene with 4 to 11 carbon atoms and at least 4 carbon atoms between the two free valencies and each of Y and Y' individually is a direct bond or the group $-CH_2-$, $-CH_2-CH_2-$, $-CH=CH-$, or $C\equiv C-$; the group $R^1R^2N-Q-CH_2-$ is attached to the 3- or 4-position of ring A and the symbol R designates that the ring to which it is attached is unsubstituted or is substituted with at least one of halogen, trifluoromethyl, cyano, nitro, lower alkyl or lower alkoxy, and their pharmaceutically acceptable acid addition salts.

These compounds have valuable pharmacological properties. In particular, they have a pronounced antifungal activity and exhibit synergistic effects in combination with known antifungally-active substances which inhibit fungal sterol biosynthesis such as ketoconazole and terbinafine. The compounds of formula I can accordingly be used as medicaments, especially for the control or prevention of topical or systemic infections which are caused by pathogenic fungi in mammals, human and non-human.

DETAILED DESCRIPTION OF THE INVENTION

The present invention is concerned with compounds having the formula

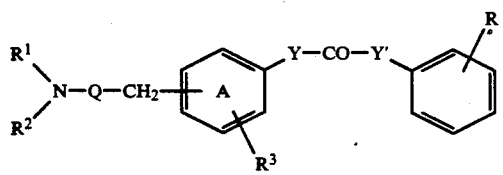

wherein each of $R^1$ and $R^2$ individually is hydrogen, lower alkyl or lower alkenyl or together are straight-chain alkylene with 2 to 4 carbon atoms, $R^3$ is hydrogen, halogen or lower alkyl, Q is alkylene with 2 to 11 carbon atoms and at least 2 carbon atoms between the two free valencies or alkenylene with 4 to 11 carbon atoms and at least 4 carbon atoms between the two free valencies and each of Y and Y' is a direct bond or the group $-CH_2-$, $-CH_2CH_2-$, $-CH=CH-$ or $-C\equiv C-$; the group $R^1R^2N-Q-CH_2-$ is attached to the 3- or 4-position of ring A and the symbol R designates that the ring to which it is attached is unsubstituted or is substituted with at least one of halogen, trifluoromethyl, cyano, nitro, lower alkyl or lower alkoxy, and their pharmaceutically acceptable acid addition salts.

These compounds have valuable pharmacological properties. In particular, they have a pronounced antifungal activity and exhibit synergistic effects in combination with known antifungally-active substances which inhibit fungal sterol biosynthesis such as ketoconazole and terbinafine. The compounds of formula I can accordingly be used as medicaments, especially for the control or prevention of topical or systemic infections which are caused by pathogenic fungi.

Fungal sterol biosynthesis inhibitors which are suitable for combination with compounds of formula I are, for example, systemic antifungally-active azoles and systemic antifungally-active allylamines.

Examples of the antifungally-active azoles include bifonazole, butoconazole, cloconazole, clotrimazole, econazole, enilconazole, fenticonazole, isoconazole, ketoconazole, miconazole, omoconazole, oxiconazole, sulconazole, tioconazole, fluconazole, itraconazole, terconazole and the like. Examples of the antifungally-active allylamines include naftifine, terbinafine and the like.

Compounds of formula I in which each of $R^1$ and $R^2$ individually is hydrogen or lower alkyl or together are straight-chain alkylene with 2 to 4 carbon atoms, $R^3$ is hydrogen, Q is unbranched alkylene with 2 or 3 carbon atoms and each of Y and Y' individually is a direct bond are known from U.S. Pat. No. 3,123,643. They are described there as intermediates for the manufacture of certain cholesterol synthesis inhibitors. No therapeutic utility is described for the intermediates themselves. It has surprisingly been found that these known compounds of formula I also have the above therapeutic activities.

Objects of the present invention are the above compounds of formula I and their pharmaceutically acceptable acid addition salts for use as therapeutically active substances; medicaments based on these substances and their manufacture; the use of these substances as medicaments in mammals, both human and non-human; the use of these substances as a prophylaxis; and for the manufacture of antifungally-active medicaments; as well as the novel compounds of formula I and their pharmaceutically acceptable acid addition salts, i.e., those compounds of formula I in which Y and Y' do not simultaneously signify a direct bond when each of $R^1$ and $R^2$ individually is hydrogen or lower alkyl or together are straight-chain alkylene with 2 to 4 carbon atoms, $R^3$ is hydrogen and Q is straight-chain alkylene with less than 4 carbon atoms, the manufacture of these novel compounds and certain intermediates for their manufacture.

The term "lower" denotes residues and compounds having a maximum of seven, preferably a maximum of four, carbon atoms. The term "alkyl" denotes straight-chain or branched, saturated hydrocarbon residues such as methyl, ethyl, propyl, isopropyl and t-butyl. The term "alkenyl" denotes straight-chain or branched hydrocarbon residues having an olefinic double bond, such as allyl and 2-butenyl. The term "alkoxy" denotes alkyl groups attached via an oxygen atom, such as methoxy and ethoxy. The term "alkylene" denotes straight-chain or branched, saturated hydrocarbon residues having two free valencies, such as dimethylene, trimethylene, tetramethylene, pentamethylene or hexamethylene. The term "alkenylene" denotes straight-chain or branched hydrocarbon residues having two free valencies and one olefinic double bond, such as 2-butene-1,4-diyl. The term "halogen" denotes fluorine, chlorine, bromine and iodine.

The term "leaving group" represents conventional leaving groups. Preferably, the leaving groups are halogen atoms, especially chlorine, bromine and iodine, and lower alkylsulphonyloxy and arylsulphonyloxy groups such as methylsulphonyloxy, benzenesulphonyloxy, p-toluenesulphonyloxy and p-chlorosulphonyloxy. The term "aryl" represents in the scope of the present invention phenyl which is unsubstituted or substituted with at least one of halogen, lower alkyl or lower alkoxy.

As discussed herein, positions 3 and 4 of ring A are shown below:

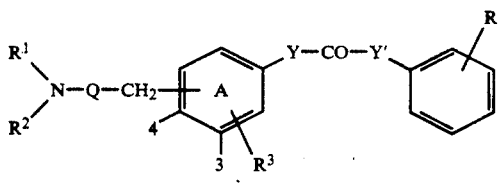

In a special embodiment the present invention is concerned with compounds of formula I above in which Q is alkylene with 4 to 11 carbon atoms and at least 2 carbon atoms between the two free valencies and $R^1$, $R^2$, $R^3$, R, Y and Y' are defined above.

Q preferably contains 4 to 7 carbon atoms and is preferably unbranched. Preferably, each of $R^1$ and $R^2$ individually is $C_{1-4}$-alkyl or $C_{3-4}$-alkenyl or together are $C_{3-4}$-alkylene. $R^3$ preferably is hydrogen. The group $R^1R^2N-Q-CH_2-$ is preferably attached to the 4-position of ring A. Y is preferably a direct bond or the group $-CH_2-$, especially a direct bond. Y' is preferably is a direct bond or the group $-CH_2-$, $-CH_2CH_2-$ or $-CH=CH-$, especially a direct bond or the group $-CH_2-$. The symbol R preferably designates that the ring to which it is attached is unsubstituted or is substituted, preferably monosubstituted or disubstituted, by halogen, especially chlorine, bromine or fluorine, trifluoromethyl, nitro or lower alkyl.

Especially preferred compounds of formula I in the scope of this aspect are:

4-[7-(Dimethylamino)heptyl]benzophenone,
4'-[7-(dimethylamino)heptyl]-3-phenylacetophenone,
4'-fluoro-4-[7-(dimethylamino)heptyl]benzophenone,
4-[7-(dimethylamino)heptyl]-4'-(trifluoromethyl)benzophenone,
2,4-difluoro-4'-[7-(dimethylamino)heptyl]benzophenone,
4-[7-(allylmethylamino)heptyl]-4'-bromobenzophenone,
4-[6-(allylmethylamino)hexyl]-4'-bromobenzophenone and
4-[7-(allylmethylamino)heptyl]benzophenone.

In a further special embodiment the present invention is concerned with compounds of formula I above in which Q is alkylene with 2 or 3 carbon atoms and at least 2 carbon atoms between the two free valencies and each of Y and Y' individually is a direct bond or the group $-CH_2-$, $-CH_2CH_2-$, $-CH=CH-$ or $-C\equiv C-$, but do not both simultaneously represent a direct bond, and $R^1$, $R^2$, $R^3$ and R are defined above.

The hydrocarbon residue Q is preferably unbranched in this case. Preferably, each of $R^1$ and $R^2$ individually is $C_{1-4}$-alkyl or $C_{3-4}$-alkenyl or together are $C_{3-4}$-alkylene. $R^3$ preferably is hydrogen. The group $R^1R^2N-Q-CH_2-$ is preferably attached to the 4-position of ring A. Preferably, Y is a direct bond and Y' is the group $-CH_2-$, $-CH_2CH_2-$ or $-CH=CH-$. The symbol R preferably represents that the ring to which it is attached is unsubstituted or is substituted, preferably monosubstituted or disubstituted, by halogen, especially chlorine, bromine or fluorine, trifluoromethyl, nitro or lower alkyl.

Especially preferred compounds of formula I in the scope of this aspect are:

3-(4-Chlorophenyl)-4'-[3-(dimethylamino)propyl]propiophenone,
3-(2-methylphenyl)-4'-[3-(dimethylamino)propyl]propiophenone and
(E)-3-phenyl-4'-[3-(1-pyrrolidinyl)propyl]acrylophenone.

The novel compounds of formula I and their pharmaceutically acceptable acid addition salts can be manufactured in accordance with the invention by a) reacting a compound having the formula

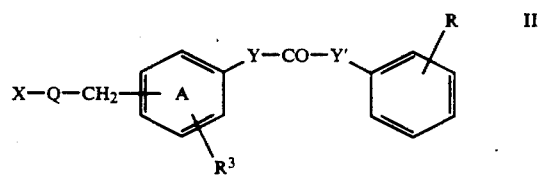

wherein X signifies a leaving group and A, $R^3$, Q, Y, Y' and R are defined above, with an amine having the formula $HNR^1R^2$, wherein $R^1$ and $R^2$ are defined above, or b) oxidizing a compound having the formula

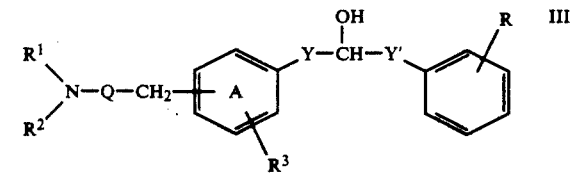

wherein A, $R^1$, $R^2$, $R^3$, Q, Y, Y' and R are defined above, or c) reacting a compound having the formula

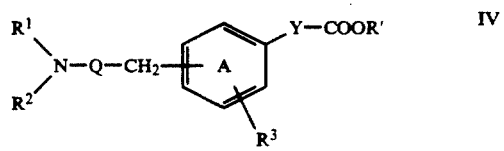

wherein R' is lower alkyl and A, $R^1$, $R^2$, $R^3$, Q and Y are defined above, with a compound having the formula

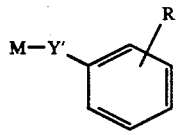 V wherein M is —MgCl, —MgBr, —MgI or —Li and Y' and R are defined above, or d) treating a compound having the formula

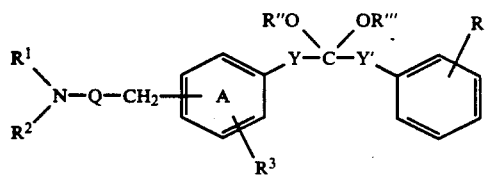 VI wherein each of R" and R'" individually is lower alkyl or together are dimethylene or trimethylene and A, $R^1$, $R^2$, $R^3$, Q, Y, Y' and R are defined above, with an aqueous acid, or e) reacting a compound having the formula X

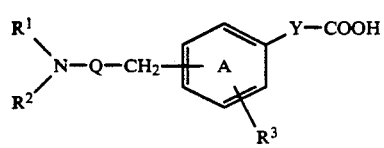 VIIa or

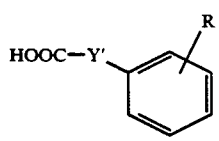 VIIb in the form of a reactive derivative in the presence of a Lewis acid with, respectively, a compound of the general formula

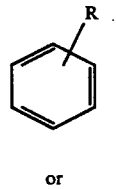 VIIIa or

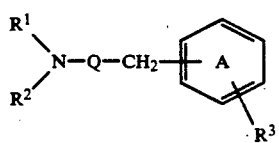 VIIIb wherein A, $R^1$, $R^2$, $R^3$, Q, Y, Y' and R are defined above, or f) reacting a compound having the formula

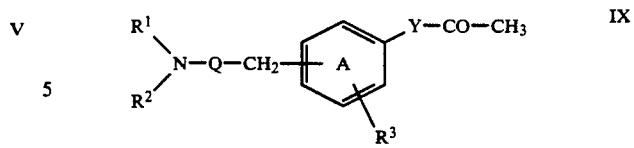 IX wherein A, $R^1$, $R^2$, $R^3$, Q and Y are defined above, in the presence of a base with a compound of the general formula

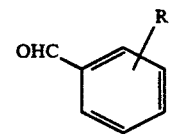 X wherein R is defined above, or g) hydrogenating a compound having the formula

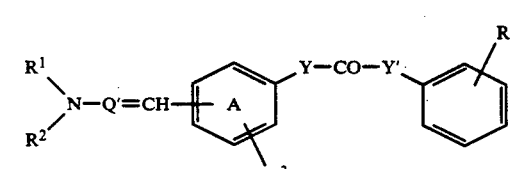

or

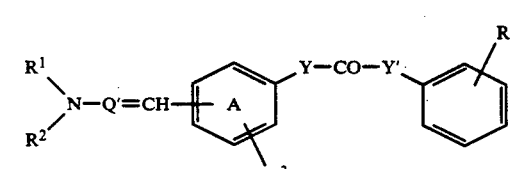 XI wherein Q' is the group Q lessened by a hydrogen atom and A, $R^1$, $R^2$, $R^3$, Q, Y, Y' and R are defined above, and h) if desired, converting a compound of formula I obtained into a pharmaceutically acceptable acid addition salt.

The reaction of a compound of formula II with an amine of the formula $HNR^1R^2$ in accordance with process variant a) can be carried out according to methods which are known to any person skilled in the art. The reaction is preferably carried out in a polar solvent and in the presence of a base as an acid-binding agent in a temperature range of about 0° C. to about 150° C. Suitable solvents are, for example, lower alcohols such as methanol and ethanol and lower dialkyl ketones such as acetone. Suitable bases are, for example, excess amine of the formula $HNR^1R^2$, tertiary amines such as triethylamine and inorganic bases such as alkali metal carbonates, alkali metal hydroxides and alkali metal alcoholates.

The oxidation of a compound of formula III in accordance with process variant b) can be carried out according to methods which are known to any person skilled in the art. The reaction is preferably carried out in an inert organic solvent and in the presence of an oxidation agent in a temperature range of about −80° C. to about room temperature (about 20° C.). Suitable solvents are, for example, chlorinated lower hydrocarbons such as methylene chloride and chloroform. Suitable oxidation agents are, for example, manganese dioxide or mixtures of dimethyl sulphoxide with oxalyl chloride, dicyclohexylcarbodiimide or acetic anhydride and a tertiary amine such as triethylamine.

The reaction of a compound of formula IV with a compound of formula V in accordance with process variant c) can be carried out according to methods which are known to any person skilled in the art. The reaction is preferably carried out in an inert solvent and in a temperature range of about −80° C. to about room temperature (about 20° C.). Suitable solvents are, for example, open-chain and cyclic ethers such as diethyl ether, methyl t-butyl ether and tetrahydrofuran and mixtures thereof.

A dilute, aqueous mineral acid, e.g. dilute hydrochloric acid, is preferably used for the treatment of a compound of formula VI with an aqueous acid in accordance with process variant d) and the treatment is preferably carried out in a temperature range of about 0° C. to about room temperature (about 20° C.).

The reaction of a reactive derivative of a compound of formula VIIa with a compound of formula VIIIa or the reaction of a reactive derivative of a compound of formula VIIb with a compound of formula VIIIb in accordance with process variant e) can be carried out according to methods which are known to any person skilled in the art. The reaction is preferably carried out in an inert solvent and in the presence of a Lewis acid in a temperature range of about 0° C. to about 100° C. Suitable solvents are, for example, halogenated lower hydrocarbons such as methylene chloride, chloroform and ethylene chloride, nitrobenzene, carbon disulphide and excess compound of formula VIIIa. Aluminium chloride is preferably used as the Lewis acid. Suitable reactive derivatives of compounds of formula VIIa or VIIb are, for example, the corresponding carboxylic acid chlorides.

The reaction of a compound of formula IX with a compound of formula X in the presence of a base in accordance with process variant f) can be carried out according to methods which are known to any person skilled in the art. The reaction is preferably carried out in a polar solvent and in a temperature range of about 0° C. to about 60° C. Suitable solvents are, for example, lower alcohols such as methanol and ethanol and mixtures thereof with water. Alkali metal carbonates and alkali metal hydroxides such as potassium carbonate and sodium hydroxide are preferably used as the bases.

The hydrogenation of a compound of formula Ia or XI in accordance with process variant g) can be carried out according to methods which are known to any person skilled in the art. The reaction is preferably carried out in a polar solvent using elemental hydrogen in the presence of a suitable hydrogenation catalyst and in a temperature range of about 0° C. to about room temperature (about 20° C.). Suitable solvents are, for example, lower alcohols such as methanol and ethanol.

Suitable catalysts are, for example, palladium or platinum on carbon, platinum oxide or Raney-nickel.

The manufacture of pharmaceutically acceptable acid addition salts of compounds of formula I in accordance with process variant h) can be carried out according to methods which are known to any person skilled in the art. Salts with pharmaceutically acceptable inorganic and organic acids come into consideration. The hydrochlorides, hydrobromides, sulphates, nitrates, citrates, acetates, succinates, fumarates, methanesulphonates and the p-toluenesulphonates are preferred acid addition salts.

The known compounds of formula I and their pharmaceutically acceptable acid addition salts can also be manufactured according to processes a)–h) above. The corresponding starting materials can be prepared as described hereinafter for the starting materials for the novel compounds of formula I.

The various compounds which are used as starting materials can be prepared in accordance with the following Reaction Schemes I-VIII and the following descriptions of the various reactions. In these Reaction Schemes $R^1$, $R^2$, $R^3$, R, R', R'', R''', A, M, Q, Q', X, Y and Y' are defined above. M' is —MgCl, —MgBr or —MgI and $\phi$ is phenyl.

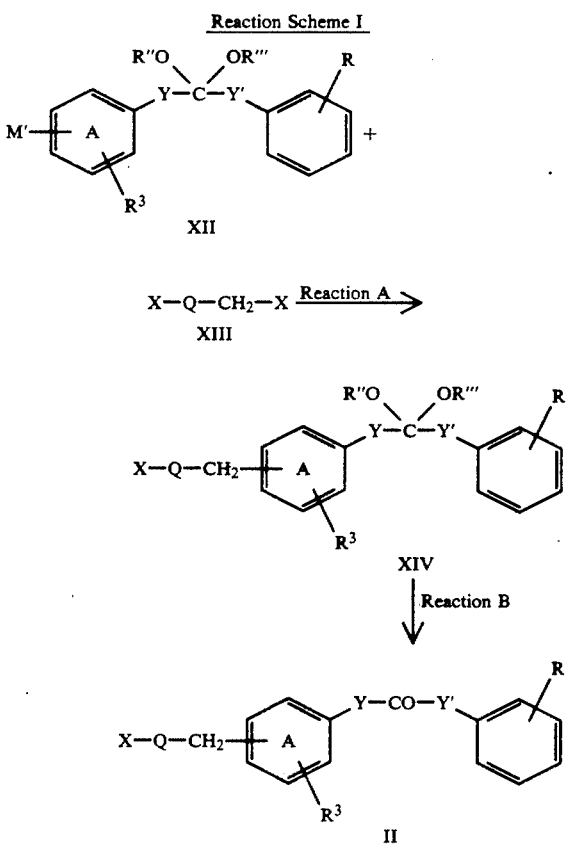

Reaction Scheme II
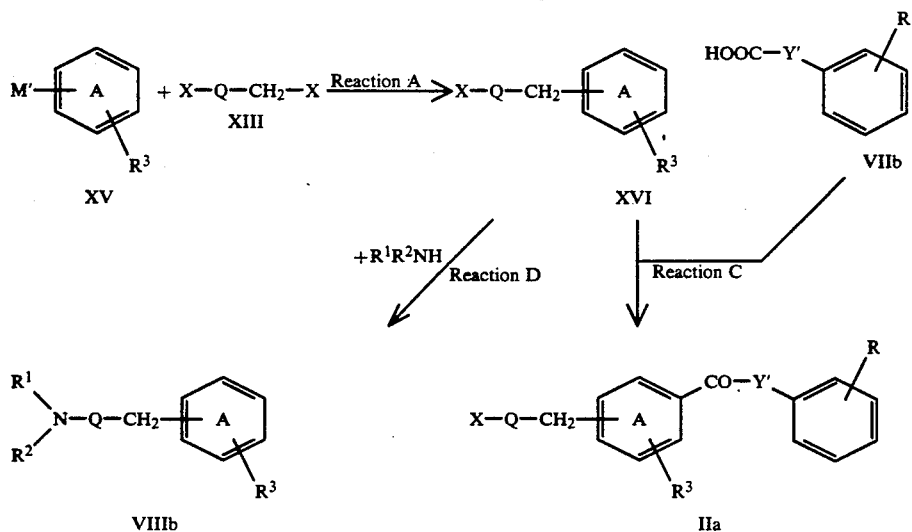
Reaction Scheme III
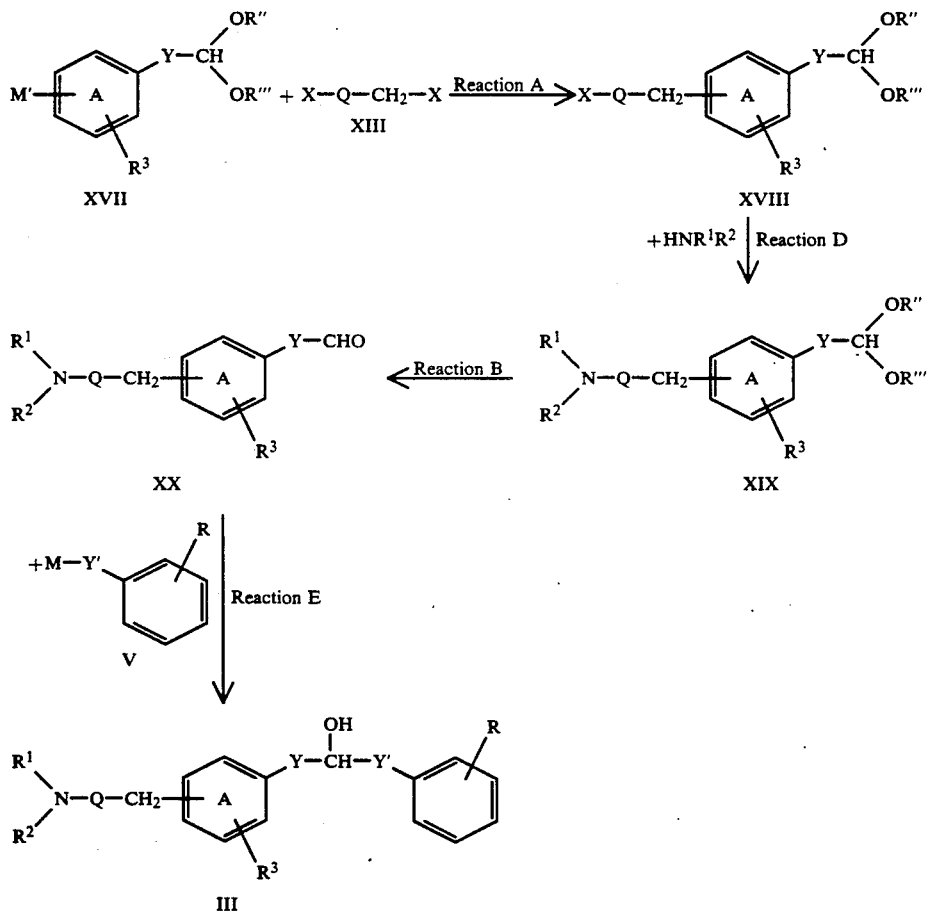

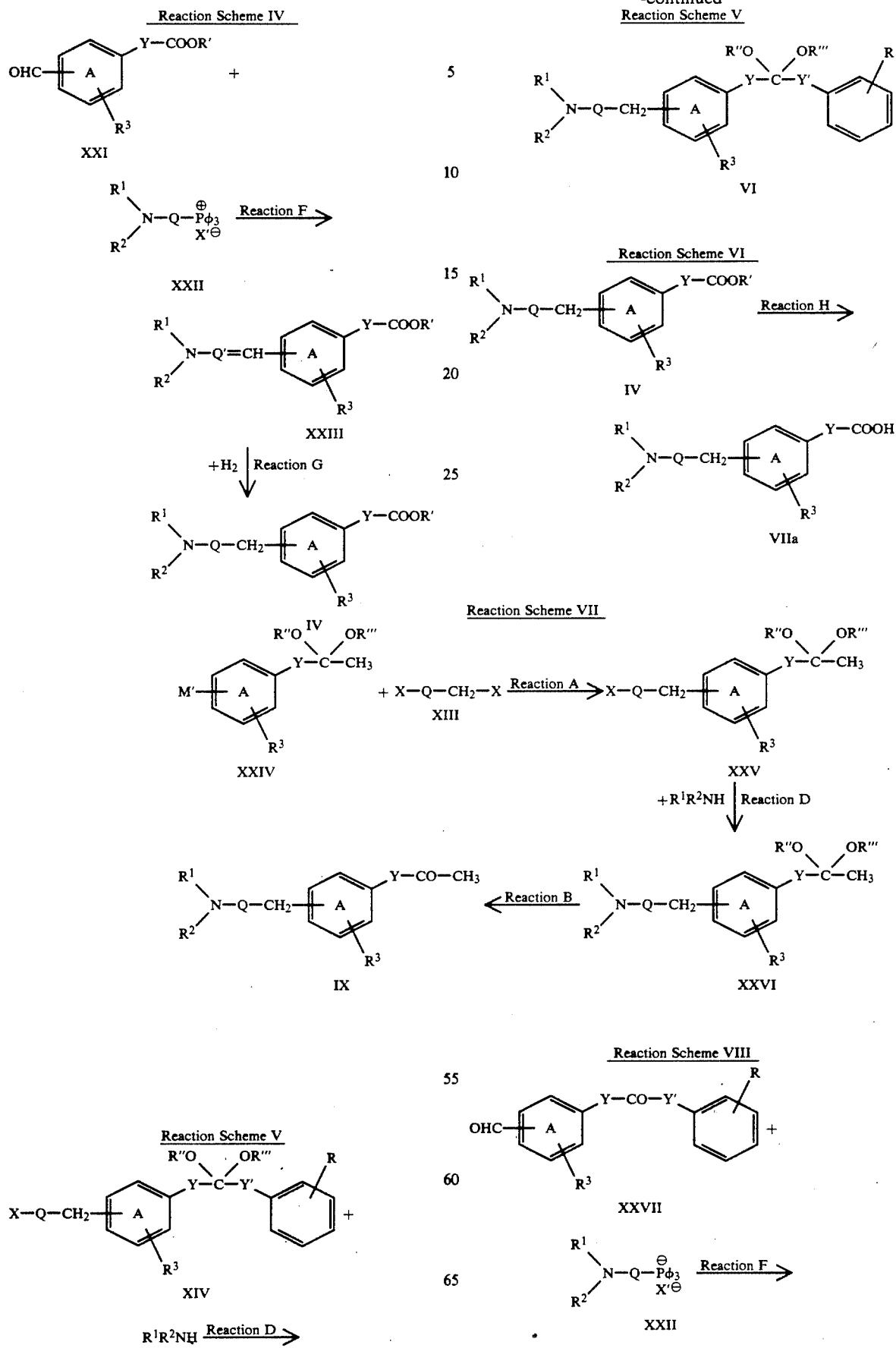

-continued
Reaction Scheme VIII

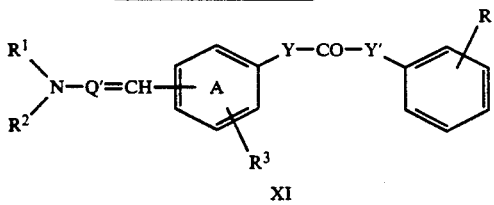

XI

REACTION A

This reaction can be carried out according to methods which are known to any person skilled in the art and is preferably carried out in an inert organic solvent in the presence of a suitable coupling reagent such as dilithium tetrachlorocuprate and in a temperature range of about 0° C. to about room temperature (about 20° C.). Suitable solvents are, for example, open-chain and cyclic ethers such as diethyl ether, dimethoxy-ethane and tetrahydrofuran.

REACTION B

This reaction can be carried out according to methods which are known to any person skilled in the art and is preferably carried out by treatment with an aqueous acid. Preferably, a dilute aqueous mineral acid, e.g. dilute hydrochloric acid, is used and the reaction is carried out in a temperature range of about 0° C. to about room temperature (about 20° C.).

REACTION C

This reaction can be carried out according to methods which are known to any person skilled in the art. The compound of formula VIIb is used in the form of a reactive derivative, for example in the form of the corresponding carboxylic acid chloride. The reaction is preferably carried out in an inert solvent and in the presence of a Lewis acid in a temperature range of about 0° C. to about 100° C. Suitable solvents are, for example, halogenated lower hydrocarbons such as methylene chloride, chloroform and ethylene chloride, nitrobenzene and carbon disulphide. Aluminium chloride is preferably used as the Lewis acid.

REACTION D

The reaction with an amine of the formula $HNR^1R^2$ can be carried out according to methods which are known to any person skilled in the art. The reaction is preferably carried out in a polar solvent and in the presence of a base as the acid-binding agent in a temperature range of about 0° C. to about 150° C. Suitable solvents are, for example, lower alcohols such as methanol and ethanol and lower dialkyl ketones such as acetone. Suitable bases are, for example, excess amine of the formula $HNR^1R^2$, tertiary amines such as triethylamine and inorganic bases such as alkali metal carbonates, alkali metal hydroxides and alkali metal alcoholates.

REACTION E

The reaction with a compound of formula V can be carried out according to methods which are known to any person skilled in the art. The reaction is preferably carried out in an inert solvent and in a temperature range of about −80° C. to about room temperature (about 20° C.). Suitable solvents are, for example, open-chain and cyclic ethers such as diethyl ether, methyl t-butyl ether and tetrahydrofuran and mixtures thereof.

REACTION F

This reaction can be carried out according to methods which are known to any person skilled in the art and is preferably carried out in an inert organic solvent in the presence of a strong base and in a temperature range of about −80° C. to about room temperature (about 20° C.). Suitable solvents are, for example, open-chain and cyclic ethers such as diethyl ether, t-butyl methyl ether and tetrahydrofuran. Suitable strong bases are, for example, lower alkali metal alcoholates such as potassium t-butylate, sodium hydride and lower alkyl-lithiums such as n-butyllithium.

REACTION G

This hydrogenation can be carried out according to methods which are known to any person skilled in the art and is preferably carried out in a polar solvent using molecular hydrogen in the presence of a suitable hydrogenation catalyst and in a temperature range of about 0° C. to about room temperature (about 20° C.). Suitable solvents are, for example, lower alcohols such as methanol and ethanol. Suitable catalysts are, for example, palladium or platinum on carbon, platinum oxide or Raney-nickel.

REACTION H

This reaction is a hydrolysis. This can be carried out according to methods which are known to any person skilled in the art and is preferably carried out by treatment with an alkali metal hydroxide such as sodium hydroxide and potassium hydroxide or with a mineral acid such as hydrochloric acid and hydrobromic acid in a polar solvent and in a temperature range of about 0° C. to about 100° C. Suitable solvents are, for example, mixtures of lower alcohols such as methanol and ethanol and water-miscible open-chain and cyclic ethers such as tetrahydrofuran with water.

The starting materials of formulae II, III and VI in which $R^1$, $R^2$, $R^3$, R, Q, Y and Y' are defined above for the novel compounds of formula I are also novel and are objects of the present invention.

As already mentioned, the compounds of formula I and their pharmaceutically acceptable acid addition salts have valuable antifungal properties. They are active against a large number of pathogenic fungi which cause topical and systemic infections, such as *Candida albicans* and *Histoplasma capsulatum*. 2,3-Epoxysqualene-lanosterol cyclase, an enzyme involved in the sterol biosynthesis of eucaryotic cells, is an essential enzyme for the fungi. Thus for example, a *S. cerevisiae* strain in which this enzyme is absent is not viable [F. Karst and F. Lacroute, Molec. Gen. Genet. 154, 269 (1977)]. The inhibitory action of the compounds of formula I on the above-mentioned enzyme from *C. albicans* was taken as the measurement for the anti-fungal activity. The inhibition can be measured, for example, by means of the method described hereinafter.

Determination of the IC50 value for the inhibition of 2,3-epoxysqualene-lanosterol cyclase from *Candida albicans*

The cells of a culture of *Candida albicans* were collected at the end of the logarithmic growth phase and washed with 100 mM phosphate buffer (pH=6.9), digestion buffer and 50 mM phosphate buffer (pH=7.4) containing 1M mannitol and 5 mM DTT.

1.0 g of these cells was suspended in 5 ml of digestion buffer, treated with 1 mg of Zymolase 100T (Seikagaku Kogyo, Japan) and 12.5 µl of β-mercaptoethanol and incubated at 30° C. for 30 minutes. The resulting protoplasts were isolated by centrifugation (10 minutes at 2500 g) and subsequently ruptured by the addition of 2 ml of 100 mM phosphate buffer (pH=6.9). By renewed centrifugation (10 minutes at 10000 g) there was obtained a cell-free extract (CFE) as the supernatant. This was diluted to 10 mg of protein per ml and the pH was brought to 6.9.

The activity of the 2,3-epoxysqualene-lanosterol cyclase in the CFE was measured by reacting $^{14}C$-squalene epoxide in the presence of n-decylpentaoxyethylene as a detergent. Titration with measured amounts of the test substance permitted the determination of the $IC_{50}$ value (concentration of test substance which reduces the enzyme activity by half).

The test was carried out as follows:

A 250 µM solution of $^{14}C$-squalene epoxide in 100 mM phosphate buffer (pH=6.9) with the addition of 1% n-decylpentaoxyethylene was prepared by ultrasonic treatment. 100 µl of this solution were treated with 20 µl of a solution of the test substance in dimethyl sulphoxide (or 20 µl of pure dimethyl sulphoxide as the control). After the addition of 880 µl of CFE the well-mixed solution was incubated at 30° for 1 hour while shaking. Subsequently, the reaction was stopped by the addition of 500 µl of 15 percent potassium hydroxide in 90 percent ethanol.

The mixture was extracted twice with 1 ml of n-hexane, the hexane was evaporated and the lipid residue was taken up in 200 µl of diethyl ether. After thin-layer chromatography on silica gel using methylene chloride as the eluent the plates were investigated using a radioactivity thin-layer scanner.

Only lanosterol was found as the radioactive product under the conditions used. Its amount was compared with the amount of radioactive lanosterol in the control.

The $IC_{50}$ values were determined graphically and are given in µg of test substance per ml. Table I contains $IC_{50}$ values determined in the above test for representative members of the class of compound defined by formula I as well as data concerning the acute toxicity in the case of subcutaneous administration to mice ($LD_{50}$ in mg/kg).

TABLE I $$\begin{array}{c} R^1 \\ \diagdown \\ N-Q-CH_2- \\ \diagup \\ R^2 \end{array} \begin{array}{c} \\ A \\ R^3 \end{array} Y-CO-Y' \begin{array}{c} R \\ \\ \end{array}$$

| No. | $R^1$ | $R^2$ | $R^3$ | Q (pos.) | Y | Y' | R | $IC_{50}$ in µg/ml | $LD_{50}$ in mg/kg s.c. |
|---|---|---|---|---|---|---|---|---|---|
| 1 | —$CH_3$ | —$CH_3$ | H | —$(CH_2)_6$-(4) | — | — | H | 0.17 | 312–625 |
| 2 | —$CH_3$ | —$CH_3$ | H | —$(CH_2)_6$-(4) | — | —$CH_2$— | H | 0.48 | |
| 3 | —$CH_3$ | —$CH_3$ | H | —$(CH_2)_6$-(4) | — | — | 4-Fluoro | 0.42 | |
| 4 | —$CH_3$ | —$CH_3$ | H | —$(CH_2)_6$-(4) | — | — | 4-Trifluoromethyl | 1.35 | |
| 5 | —$CH_3$ | —$CH_3$ | H | —$(CH_2)_6$-(4) | — | — | 2,4-Difluoro | 0.55 | |
| 6 | —$CH_3$ | —$CH_3$ | H | —$(CH_2)_2$-(4) | — | —CH=CH— | 4-Chloro | 1.20 | |
| 7 | —$CH_3$ | —$CH_3$ | H | —$(CH_2)_2$-(4) | — | $CH_2CH_2$— | 4-Chloro | 0.40 | |
| 8 | —$CH_3$ | —$CH_3$ | H | —$(CH_2)_2$-(4) | — | $CH_2CH_2$— | 4-Fluoro | 0.55 | |
| 9 | —$CH_3$ | —$CH_3$ | H | —$(CH_2)_2$-(4) | — | $CH_2CH_2$— | 2-Methyl | 0.11 | |
| 10 | —$CH_3$ | —$CH_3$ | H | —$(CH_2)_2$-(4) | — | $CH_2CH_2$— | 3-Chloro | 0.44 | |
| 11 | —$CH_3$ | —$CH_3$ | H | —$(CH_2)_2$-(4) | — | $CH_2CH_2$— | 4-Nitro | 0.28 | |
| 12 | —$(CH_2)_4$— | | H | —$(CH_2)_2$-(4) | — | —CH=CH— | H | 0.25 | |
| 13 | —$(CH_2)_4$— | | H | —$(CH_2)_2$-(4) | — | —$CH_2CH_2$— | H | 0.40 | |
| 14 | —$CH_3$ | —$CH_3$ | H | —$(CH_2)_2$-(4) | — | — | H | 5 | |
| 15 | —$CH_3$ | —$CH_3$ | H | —$(CH_2)_7$-(4) | — | — | H | 0.41 | |
| 16 | —$CH_3$ | —$CH_3$ | H | —$(CH_2)_7$-(4) | — | — | H | 0.14 | |
| 17 | —$CH_3$ | —$CH_3$ | H | —$(CH_2)_6$-(4) | — | — | 4-Chloro | 0.49 | |
| 18 | —$CH_3$ | —$CH_3$ | H | —$(CH_2)_6$-(4) | — | — | 4-Bromo | 0.86 | |
| 19 | —$CH_3$ | —$CH_3$ | H | —$(CH_2)_6$-(4) | — | — | 2,4-Dichloro | 0.75 | |
| 20 | —$CH_3$ | —$CH_3$ | H | —$(CH_2)_6$-(4) | — | — | 4-Cyano | 0.26 | |
| 21 | —$CH_2$—CH=$CH_2$ | —$CH_3$ | H | —$(CH_2)_6$-(4) | — | — | H | 0.05 | |
| 22 | —$CH_2$—CH=$CH_2$ | —$CH_3$ | H | —$(CH_2)_6$-(4) | — | — | 4-Bromo | 0.19 | |
| 23 | —$CH_2$—CH=$CH_2$ | —$CH_3$ | H | —$(CH_2)_6$-(4) | — | — | 4-Cyano | 0.06 | |
| 24 | —$CH_2$—CH=$CH_2$ | —$CH_3$ | H | —$(CH_2)_5$-(4) | — | — | 4-Bromo | 0.095 | 312–625 |
| 25 | —$CH_3$ | —$CH_3$ | H | —$(CH_2)_5$-(4) | — | — | 4-Bromo | 0.92 | |
| 26 | —$CH_3$ | —$CH_3$ | H | —$(CH_2)_5$-(4) | — | — | 3-Bromo | 0.42 | |
| 27 | —$CH_3$ | —$CH_3$ | H | —$(CH_2)_5$-(4) | — | — | 2-Methyl | 0.16 | |
| 28 | —$CH_3$ | —$CH_3$ | H | —$(CH_2)_5$-(4) | — | — | 4-Nitro | 0.21 | |
| 29 | —$CH_3$ | —$CH_3$ | H | —$(CH_2)_5$-(4) | — | — | 2-Chloro | 0.11 | |

The already mentioned synergistic activity of the compounds of formula I and their pharmaceutically acceptable acid addition salts in combination with fungal sterol biosynthesis inhibitors such as ketoconazole can be demonstrated, for example, by means of the agar dilution method. For this purpose there was used casitone agar and inocula (10 cells/ml) of cultures of Candida albicans which are 48 hours old. The test substances (TS, compounds of formula I) were applied in concentrations of 80–1.25 µg/ml and the sterol biosynthesis inhibitors (SBI) were applied in concentrations of 20–0.001 µg/ml, with the dilution steps being in each case 1:2. The cultures were incubated at 37° C. for 2 days. The minimum inhibitory concentrations (MIC) of the various active substances were then determined in the case of the application alone and in the case of the combined application and the fractional inhibitory concentration (FIC) was calculated according to the following formula from the MIC values determined:

$$FIC = \frac{MIC\ (TS\ alone)}{MIC\ (TS\ in\ combination)} + \frac{MIC\ (SBI\ alone)}{MIC\ (SBI\ in\ combination)}$$

A synergistic activity is present when the FIC is <0.5. The data in Table II for compound 1 (according to Table I), a representative member of the class of compound defined by formula I, in combination with ketoconazole, a representative sterol biosynthesis inhibitor, confirms the synergistic activity.

TABLE II

| C. albicans | MIC in μg/ml | | | |
|---|---|---|---|---|
| | Compound 1 Ketoconazole alone | Compound 1 in combination | Ketoconazole | FIC |
| $H_{12}$ | 20    5 | 2.5 | 0.3 | 0.19 |
| $H_{29}$ | 10    1.29 | 1.2 | 0.075 | 0.19 |
| $H_{42}$ | 20    5 | 1.2 | 0.15 | 0.005 |
| $B_5$ | 20    0.15 | 1.2 | 0.075 | 0.53 |
| $B_4$ | 20    2.5 | 1.2 | 0.15 | 0.06 |

The compounds of formula I and their pharmaceutically acceptable acid addition salts can be used as medicaments in mammals human or non-human, for example, in the form of pharmaceutical preparations for enteral, parenteral or topical application. They can be administered, for example, perorally, for example, in the form of tablets, coated tablets, dragees, hard and soft gelatine capsules, solutions, emulsions or suspensions, rectally, for example, in the form of suppositories, parenterally, for example, in the form of injection solutions or infusion solutions, or topically, for example, in the form of ointments, creams or oils.

The manufacture of the pharmaceutical preparations can be effected in a manner which is familiar to any person skilled in the art by bringing the described compounds of formula I and their pharmaceutically acceptable acid addition salts, optionally in combination with other therapeutically valuable substances, for example the mentioned sterol biosynthesis inhibitors, into a galenical dosage form together with suitable, non-toxic, inert, therapeutically compatible solid or liquid carrier materials and, if desired, the usual pharmaceutical adjuvants.

Suitable carrier materials are not only inorganic carrier materials, but also organic carrier materials. Thus, lactose, maize starch or derivatives thereof, talc, stearic acid or its salts can be used, for example, as carrier materials for unit dosage forms such as tablets, coated tablets, dragees and soft or hard gelatine capsules. Suitable carrier materials for soft gelatine capsules are, for example, vegetable oils, waxes, fats and semi-solid and liquid polyols (depending on the nature of the active substance no carriers are, however, required in the case of soft gelatine capsules). Suitable carrier materials for the manufacture of solutions and syrups for their respective unit dosage form are, for example, water, polyols, saccharose, invert sugar and glucose. Suitable carrier materials for injection solution unit dosage forms are, for example, water, alcohols, polyols, glycerol and vegetable oils. Suitable carrier materials for unit dosage suppositories are, for example, natural or hardened oils, waxes, fats and semi-liquid or liquid polyols. Suitable carrier materials for unit dosage topical preparations are glycerides, semi-synthetic and synthetic glycerides, hydrogenated oils, liquid waxes, liquid paraffins, liquid fatty alcohols, sterols, polyethylene glycols and cellulose derivatives.

The usual stabilizing, preserving, wetting and emulsifying agents, consistency-improving agents, flavour-improving agents, salts for varying the osmotic pressure, buffer substances, solubilizers, colouring and coating agents and antioxidants come into consideration as pharmaceutical adjuvants.

The dosage of the compounds of formula I can vary within wide limits depending on the pathogenic fungi to be controlled, the age and the individual condition of the patient and on the mode of application and will, of course, be fitted to the individual requirements in each particular case. In the case of adult patients a daily dosage of about 0.01 g to about 4 g, especially about 0.05 g to about 2 g, comes into consideration for the prevention and control of topical and systemic infections by pathogenic fungi. Depending on the dosage it is convenient to administer the daily dosage in several dosage units. In the case of combination therapy a daily dosage of about 0.01 g to about 2 g, especially about 0.02 g to about 1 g, of a compound of formula I and of about 0.02 g to about 0.2 g of a sterol biosynthesis inhibitor comes into consideration.

The pharmaceutical mono-preparations conveniently contain about 10–1000 mg, preferably 50–500 mg, of a compound of formula I in unit dosage form. The combination preparations conveniently contain about 10–500 mg, preferably 20–250 mg, of a compound of formula I and about 50–100 mg of a sterol biosynthesis inhibitor.

The following Examples serve to illustrate the present invention in more detail. They are, however, not intended to limit its scope in any manner. The examples 1–14 were actually conducted as set forth below. All temperatures are given in degrees Celsius. All ratios are at volume/volume unless otherwise stated.

EXAMPLE 1 a) 9.3 g of 1,6-dibromohexane and 5 g of triphenylphosphine were stirred under argon at 100° for 1 hour. The reaction mixture was subsequently cooled and chromatographed on 90 g of silica gel with methylene chloride/methanol 95:5. The 6-bromohexyl-phosphonium bromide (6.37 g, 65%) obtained was treated with 35 ml of a 33 percent solution of dimethylamine in ethanol and stirred at room temperature for 24 hours under argon. The solution was evaporated and the residue was dried carefully in a high vacuum. The 6-(dimethylamino)hexyl-triphenylphosphonium bromide hydrobromide obtained was suspended in 50 ml of tetrahydrofuran, whereupon the suspension was treated portionwise at 0° with 2.09 g of potassium t-butylate. The mixture was stirred at 0° for 15 minutes. Subsequently, a solution of 1.86 g of 4-benzoyl-benzaldehyde [Tetrahed. Lett. 24, 4287 (1983)] in 10 ml of tetrahydrofuran was added thereto at 0° and the mixture was stirred at room temperature for 18 hours. The reaction mixture was evaporated. The residue was taken up in 100 ml of 1N hydrochloric acid and extracted three times with 100 ml of ether. The aqueous phase was made basic with 2N sodium hydroxide solution while cooling with ice and extracted three times with methylene chloride. The organic phases were dried over magnesium sulphate and evaporated. The crude product obtained was chromatographed on 100 g of neutral aluminium oxide (activity grade III) with methylene chloride/ethyl acetate 95:5. After evaporation there were obtained 1.98 g (31%) of 4-[(Z)-7-(dimethylamino)-1-heptenyl]benzophenone as a colourless oil.

$^1$H—NMR (CDCl$_3$): 1.3–1.8 (m; 6H); 2.22 (s; 6H); 2.29 (t; J=8 Hz; 2H); 2.35 (m; 2H), 5.80 (dxt; J=12 Hz; 1H); 6.48 (dxt; J=12 Hz; J=2 Hz; 1H); 7.39 (d; J=8 Hz; 2H); 7.4–7.8 (m; 7H) ppm.

b) 1.12 g of 4-[(Z)-7-(dimethylamino)-1-heptenyl]benzophenone were dissolved in 30 ml of methanol, 20 mg of 5 percent palladium on carbon were added thereto and the suspension was stirred under hydrogen at normal pressure and room temperature for 2.5 hours. The reaction mixture was filtered through silica gel and the filtrate was evaporated. There were obtained 1.10 g (98%) of 4-[7-(dimethylamino)heptyl]benzophenone as a colourless oil.

$^1$H—NMR (CDCl$_3$): 1.3–1.6 (m; 8H); 1.67 (g; J=7,5 Hz; 2H); 2.23 (s; 6H); 2.29 (t; J=8 Hz; 2H); 2.69 (t; J=7,5 Hz; 2H); 7.3–7.9 (m; 9H) ppm.

EXAMPLE 2 a) 2.47 g of potassium t-butylate were added to a suspension of 5.06 g of 6-(dimethylamino)hexyl-triphenylphosphonium bromide hydrobromide (see Example 1 a) in 50 ml of tetrahydrofuran at 0° under argon. To this suspension was added dropwise within 15 minutes a solution of 1.64 g of methyl p-formylbenzoate in 20 ml of tetrahydrofuran. The reaction mixture was stirred at room temperature for 18 hours and then evaporated. The residue was dissolved in 100 ml of 1N hydrochloric acid and the aqueous phase was washed three times with 100 ml of diethyl ether. The aqueous phase was made basic with solid potassium carbonate and extracted three times with 100 ml of ether. The ethereal phases were dried over magnesium sulphate and evaporated. The residue was chromatographed on 100 g of silica gel with methylene chloride/methanol/ammonium hydroxide 100:10:1. There were obtained 880 mg (32%) of methyl 4-[(Z)-7-(dimethylamino)-1-heptenyl]benzoate as a colourless oil.

b) 0.88 g of methyl 4-[(Z)-7-(dimethylamino)-1-heptenyl]benzoate was dissolved in 20 ml of ethanol, 20 mg of 5 percent palladium on carbon were added thereto and the suspension was stirred under hydrogen at normal pressure and room temperature for 2 hours. The reaction mixture was filtered through siliceous earth and the filtrate was evaporated. There was obtained 0.85 g (95%) of methyl 4-[7-(dimethylamino)heptyl]benzoate as a colourless oil.

c) A solution of benzylmagnesium bromide in 20 ml of ether (prepared from 74 mg of magnesium and 524 mg of benzyl bromide) was added dropwise within 30 minutes to a solution of 0.85 g of methyl 4-[7-(dimethylamino)heptyl]benzoate in 20 ml of tetrahydrofuran at −78° under argon. The reaction mixture was stirred at −78° for 2 hours, then poured into 50 ml of a saturated ammonium chloride solution and extracted three times with 50 ml of ethyl acetate. The combined organic phases were washed with 100 ml of a saturated sodium chloride solution, dried over magnesium sulphate and evaporated. After chromatography of the residue on 100 g of silica gel with methylene chloride/methanol/ammonium hydroxide 100:10:1 there were obtained 340 mg (35%) of 4'-[7-(dimethylamino)heptyl]-2-phenylacetophenone as a yellowish oil.

$^1$H—NMR (CDCl$_3$): 1.3–1.7 (m,10H); 2.40 (s,6H); 2.52 (t,J=8 Hz,2H); 2.64 (t,J=7 Hz,2H); 4.26 (s,2H); 7.3–7.4 (m,7H); 7.93 (d,J=8 Hz,2H) ppm.

EXAMPLE 3

In analogy to Example 2c), from methyl 4-[7-(dimethylamino)heptyl]benzoate and a) phenethylmagnesium bromide there was obtained 4'-[7-(dimethylamino)heptyl]-3-phenylpropiophenone as a colourless oil (yield 35%).

$^1$H—NMR (CDCl$_3$): 1.3–1.7 (m,10H); 2.20 (s,6H); 2.1–2.3 (m,2H); 2.64 (t,J=8 Hz,2H); 3.0–3.4 (m,4H); 7.2–7.4 (m,7H); 7.88 (d,J=8 Hz,2H) ppm;

b) p-(trifluoromethyl)phenylmagnesium bromide there was obtained 4-[7-(dimethylamino)heptyl]-4'-(trifluoromethyl)benzophenone as a colourless oil (yield 40%).

$^1$H—NMR (CDCl$_3$): 1.3–1.7 (m,10H); 2.24 (s,6H); 2.28 (t,J=8 Hz,2H); 2.69 (t,J=8 Hz, 2H); 7.29 (d,J=9 Hz,2H); 7.7–7.9 (m,6H) ppm.

MS: 391 (1.5%, M+); 372 (1%); 235 (2.5%); 173 (3.8%); 145 (4.5%); 58 (100%).

EXAMPLE 4 a) 1.2 g of methyl 4-[7-(dimethylamino)heptyl]benzoate were treated with 25 ml of methanol and 10 ml of 20 percent sodium hydroxide in water, whereupon the mixture was heated under reflux for 2 hours. After cooling to 0° the pH of the solution was adjusted to 5 with acetic acid. The precipitated material was filtered off under suction and dried overnight in a high vacuum at about 6.7 Pa. There was obtained 0.97 g (85%) of 4-[7-(dimethylamino)heptylbenzoic acid.

b) This material was suspended in 20 ml of methylene chloride, treated with 1.2 ml of oxalyl chloride, the reaction mixture was stirred at room temperature for 2 hours and then evaporated. The crude acid chloride was dried in a high vacuum, dissolved in 3 ml of fluorobenzene and the solution was cooled to 0°. 760 mg of aluminium chloride were added to this solution and the mixture was stirred at 0° for 30 minutes and then at room temperature for 2 hours. The reaction mixture was diluted with 50 ml of methylene chloride and washed twice with 50 ml of 2N sodium hydroxide solution. The methylene chloride phase was dried over magnesium sulphate and evaporated. The crude product was purified on 100 g of silica gel with methylene chloride/methanol/ammonium hydroxide 90:10:1. There was obtained 0.5 g (40%) of 4-[7-(dimethylamino)-heptyl]-4'-fluorobenzophenone as a colourless oil.

$^1$H—NMR (CDCl$_3$): 1.3–1.7 (m,10H); 2.23 (s,6H); 2.26 (t,J=7,5 Hz,2H); 2.68 (t,J=7,5 Hz,2H); 7.1–7.2 (m,2H); 7.28 (d,J=8 Hz,2H); 7.70 (d,J=8 Hz,2H), 7.7–7.9 (m,2H) ppm.

EXAMPLE 5

In analogy to Example 4b), from 4-[7-(dimethylamino)-heptyl]benzoic acid and 1,3-difluorobenzene there was obtained 2,4-difluoro-4'-[7-(dimethylamino)heptyl]benzophenone as a colourless oil (yield 32%). $^1$H—NMR (CDCl$_3$): 1.3–1.7 (m, 10H); 2.25 (s, 6H); 2.28 (t,J=7 Hz, 2H); 2.67 (t,J=8 Hz, 2H); 6.8–7.8 (m, 7H) ppm.

EXAMPLE 6

A solution of 6.1 g of 2-(p-bromophenyl)-2-phenyl-1,3-dioxolane (German Offenlegungsschrift No. 2509474) in 50 ml of tetrahydrofuran was added dropwise under argon within 3 minutes to a suspension of 486 mg of magnesium shavings in 10 ml of tetrahydrofuran. The brown solution obtained was stirred at room temperature for 1 hour, then cooled to 0° and added dropwise at 0° within one hour to a solution of 5.12 g of dibromohexane and 0.1 mmol of dilithium tetrachlorocuprate (Synthesis, 1971, 303). The mixture was stirred at room temperature for 18 hours and evaporated. The residue was treated with 100 ml of a saturated ammonium chloride solution and extracted three times with 100 ml of ether. The organic phases were dried over magnesium sulphate and evaporated. The residue, containing 2-[4-(6-bromohexyl)phenyl]-2-phenyl-1,3-dioxolane, was treated with 25 ml of a 33 percent solution of dimethylamine in ethanol and stirred at room temperature for 24 hours. The solution was concentrated; the residue, containing 2-[4-[6-(dimethylamino)hexyl]-phenyl]-2-phenyl-1,3-dioxolane, was taken up in 100 ml of 1N hydrochloric acid and extracted three times with 100 ml of ether. The aqueous phase was made basic with 2N sodium hydroxide solution while cooling with ice and extracted three times with 100 ml of ether. The organic phases were dried over magnesium sulphate and evaporated. The crude product was purified by distillation in a bulb-tube oven at 180°–190° and about 6.7 Pa. There were obtained 2.55 g (41%) of 4-[6-(dimethylamino)hexyl]benzophenone as a light yellow oil.

This oil was dissolved in 5 ml of ethanol and added to a hot solution of 0.956 g of fumaric acid in 20 ml of ethanol. After the addition of 50 ml of ether and cooling to 0° the colourless crystals were filtered off under suction, washed with ether and dried. There were obtained 3 g (85%) of 4-[6-(dimethylamino)hexyl]benzophenone fumarate 1:1 with a m.p. of 87°–89°.

EXAMPLE 7 a) 15 g of 4-(3-bromopropyl)acetophenone and 10.8 ml of pyrrolidine were dissolved in 60 ml of ethanol and warmed to 40° for 24 hours. The reaction mixture was then evaporated and the residue was treated with 250 ml of ethyl acetate and 150 ml of semi-saturated sodium chloride solution, whereupon extraction was carried out. The aqueous phase was extracted again with 250 ml of ethyl acetate and the organic phases were again washed with 150 ml of semi-saturated sodium chloride solution. The combined organic extracts were dried over magnesium sulphate and evaporated. There were obtained 13.8 g (96%) of 4'-[3-(1-pyrrolidinyl)propyl]acetophenone as a brownish liquid; mass spectrum m/e: M+ 431 (6.4), 84 (100), 42 (10.9).

b) 4 g of 4'-[3-(1-pyrrolidinyl)propyl]acetophenone and 2 g of benzaldehyde were dissolved in 80 ml of methanol and treated with a solution of 9.55 g of potassium carbonate in 38 ml of water within 15 minutes while cooling with an ice bath. The mixture was then left to react at room temperature for 18 hours and at about 40° for a further 18 hours. The reaction mixture was taken up in 200 ml of ethyl acetate and extracted with 100 ml of water. The aqueous phase was again extracted with 200 ml of ethyl acetate and the organic phases were again extracted with 100 ml of semi-saturated sodium chloride solution. The combined organic phases were dried over magnesium sulphate and evaporated. The residue was chromatographed on silica gel with acetone. There were obtained 4.5 g (81%) of (E)-3-phenyl-4'-[3-(1-pyrrolidinyl)propyl]acrylophenone as a yellow oil; mass spectrum m/e: M+ 319 (7.1), 131 (1.4), 84 (100), 42 (7.5). For the formation of the hydrochloride, the free amine was dissolved in a small amount of ethanol and treated with 10M ethanolic hydrochloric acid solution. After recrystallization of the resulting material from isopropanol there was obtained the pure hydrochloride; m.p. 211°–213°.

EXAMPLE 8

4.1 g of 4-[3-(dimethylamino)propyl]acetophenone and 3.1 g of 4-chlorobenzaldehyde were dissolved in 80 ml of methanol and treated at room temperature within 15 minutes with a solution of 6.4 g of sodium hydroxide in 32 ml of water. The mixture was then left to stir at room temperature for 48 hours. For the working-up, the mixture was poured on to 150 ml of ice-water. The separated crystals were filtered off under suction, washed three times with 30 ml of water each time and dried at 40° under reduced pressure. There were obtained 6.36 g (97%) of (E)-3-(4-chlorophenyl)-4'-[3-(dimethylamino)propyl]acrylophenone; m.p. 83°–86°.

The 4-[3-(dimethylamino)propyl]acetophenone was prepared in analogy to Example 7a).

EXAMPLE 9

3 g of (E)-3-(4-chlorophenyl)-4'-[3-(dimethylamino)propyl]acrylophenone were dissolved in 100 ml of ethanol and, after the addition of 300 mg of 5 percent palladium on carbon, hydrogenated. After the uptake of the theoretical amount of hydrogen the catalyst was filtered off and the filtrate was evaporated. The residue was dissolved in ethanol and converted using 10M ethanolic hydrochloric acid solution into the hydrochloride which was precipitated by the addition of hexane. After recrystallization from ethyl acetate/ethanol 5:1 there were obtained 1.44 g (43%) of 3-(4-chlorophenyl)-4'-[3-(dimethylamino)propyl]propiophenone hydrochloride; m.p. 161°–164°.

EXAMPLE 10

The compounds listed hereinafter were manufactured in analogy to Examples 7b) and 8:

a) (E)-3-(4-Methylphenyl)-4'-[3-(dimethylamino)propyl]acrylophenone; m.p. 76.5°–77.5°;

b) (E)-3-(4-isopropylphenyl)-4'-[3-(dimethylamino)propyl]acrylophenone; m.p. 44°–45°;

c) (E)-3-(4-methoxyphenyl)-4'-[3-(dimethylamino)propyl]acrylophenone as an oil; $^1$H—NMR (CDCl$_3$, 400 MHz): 2.24 (s, 6H); 3.86 (s, 3H) ppm;

d) (E)-3-[4-(trifluoromethyl)phenyl]-4'-[3-(dimethylamino)propyl]acrylophenone; m.p. 71.5°–73.5°;

e) (E)-3 (3-methylphenyl)-4'-[3-(dimethylamino)propyl]acrylophenone as an oil; $^1$H—NMR (CDCl$_3$, 400 MHz): 2.25 (s, 6H); 2.40 (s, 3H) ppm;

f) (E)-3-(4-nitrophenyl)-4'-[3-(dimethylamino)propyl]acrylophenone; m.p. 97°–99°;

g) (E)-3-(3-chlorophenyl)-4'-[3-(dimethylamino)propyl]acrylophenone as a wax; mass spectrum m/e: M+ 327 (1.1), 205 (0.8), 143 (0.9), 58 (100);

h) (E)-3-phenyl-4'-[3-(ethylmethylamino)propyl]acrylophenone as an oil; mass spectrum m/e: M+ 307 (4), 72 (100) (the 4-[3-(ethylmethylamino)propyl]acetophenone used as the starting material was prepared in analogy to Example 7a));

i) (E)-3-(4-t.butylphenyl)-4'-[3-(dimethylamino)propyl]acrylophenone hydrochloride; m.p. 217°–219° (from ethanol);

j) (E)-3-(3,5-dichlorophenyl)-4'-[3-(dimethylamino)propyl]acrylophenone hydrochloride; m.p. >230° (decomposition);

k) (E)-3-(4-fluorophenyl)-4'-[3-(dimethylamino)-propyl]acrylophenone hydrochloride; m.p. 219°–220.5° (from ethanol);

l) (E)-3-(2-methylphenyl)-4'-[3-(dimethylamino)-propyl]acrylophenone hydrochloride; m.p. 150.5°–152° (from ethanol/toluene).

EXAMPLE 11

The compounds listed hereinafter were manufactured in analogy to Example 9:

a) 3-(4-Methylphenyl)-4'-[3-(dimethylamino)propyl]-propiophenone as an oil; $^1$H—NMR (CDCl$_3$, 400 MHz): 2.22 (s, 6H); 2.32 (s, 3H) ppm;

b) 3-(4-isopropylphenyl)-4'-[3-(dimethylamino)-propyl]propiophenone as an oil; mass spectrum m/e: M+ 337 (5), 133 (4), 58 (100);

c) 3-(4-methoxyphenyl)-4'-[3-(dimethylamino)-propyl]propiophenone as a syrup; mass spectrum m/e: M+ 325 (4), 121 (9), 58 (100);

d) 3-[4-(trifluoromethyl)phenyl]-4'-[3-(dimethylamino)propyl]propiophenone as an oil; mass spectrum m/e: M+ 363 (2), 159 (3), 58 (100);

e) 3-(3-methylphenyl)-4'-[3-(dimethylamino)propyl]-propiophenone as an oil; mass spectrum m/e: M+ 309 (10.4), 145 (3.8), 105 (7.0), 58 (100);

f) 3-(3-chlorophenyl)-4'-[3-(dimethylamino)propyl]-propiophenone as an oil; mass spectrum m/e: M+ 329 (1.0), 125 (2.5), 58 (100);

g) 3-phenyl-4'-[3-(ethylmethylamino)propyl]propi-ophenone as a syrup; mass spectrum m/e: M+ 309 (6), 294 (1), 91 (6), 72 (100);

h) 3-(4-t-butylphenyl)-4'-[3-(dimethylamino)propyl]-propiophenone as an oil; mass spectrum m/e: M+ 351 (34.7), 131 (32.8), 91 (34.5), 58 (100);

i) 3-(4-fluorophenyl)-4'-[3-(dimethylamino)propyl]-propiophenone as a syrup; mass spectrum m/e: M+ 313 (3), 109 (11), 58 (100);

j) (3-(2-methylphenyl)-4'-[3-(dimethylamino)propyl]-propiophenone; m.p. 145°–147° (from tetrahydrofuran);

k) 3-phenyl-4'-[3-(1-pyrrolidinyl)propyl]propiophenone as a syrup; mass spectrum m/e: M+ 321 (7), 91 (6), 84 (100).

EXAMPLE 12

The compounds listed hereinafter were manufactured in analogy to Example 1:

a) 4-[5-(Dimethylamino)pentyl]benzophenone as a colourless oil (yield 96%).

Mass spectrum m/e: M+ 295 (2%, M+), 100 (3%), 58 (100%).

b) 4-[8-(Dimethylamino)octyl]benzophenone as a colourless oil (yield 88%).

Mass spectrum m/e: M+ 337 (2%, M+), 149 (2.8%), 105 (3.3%), 58 (100%).

EXAMPLE 13 a) A solution of 13.3 g of p-toluenesulphonyl chloride in 100 ml of methylene chloride was added dropwise under argon at 0° C. within 1 hour to a solution of 10 g of 7-chloroheptanol (Rec. Trav. Chim. Pays-Bas, 99, 87 (1980)) and 18.7 ml of triethylamine in 100 ml of methylene chloride. The reaction mixture was stirred at room temperature for 6 hours and then washed twice with 200 ml of 2N hydrochloric acid each time, twice with 200 ml of saturated sodium bicarbonate solution each time and once with 200 ml of saturated sodium chloride solution. The organic phase was dried over magnesium sulphate and concentrated. The crude 7-chloroheptyl p-toluenesulphonate (19.5 g, 96%) was dissolved in 40 ml of tetrahydrofuran with 0.6 mmol of dilithium tetrachlorocuprate. This solution was cooled to 0° C. under argon. A solution of phenylmagnesium bromide (prepared from 3.1 g of magnesium shavings and 20 g of bromobenzene in 80 ml of tetrahydrofuran) was then added dropwise thereto within two hours. The reaction mixture was stirred at room temperature for 18 hours and evaporated.

The residue was treated with 200 ml of a saturated ammonium chloride solution and extracted three times with 200 ml of ether each time. The organic phases were dried over magnesium sulphate and evaporated. The residue was distilled in a high vacuum at 100°–110° C. and about 13.4 Pa. There were obtained 13 g (86%) of 7-chloroheptylbenzene as a colourless liquid.

b) 1.07 g of 7-chloroheptylbenzene and 0.89 g of 4-chlorobenzoyl chloride were dissolved in 10 ml of nitrobenzene and treated with 0.82 g of aluminium chloride under argon and while cooling with ice. The mixture was then stirred at room temperature for 18 hours, taken up in 100 ml of ice-cold 2N hydrochloric acid solution and extracted three times with 50 ml of ether each time. The organic phases were washed with 50 ml of a 10 percent sodium bicarbonate solution and 50 ml of a saturated sodium chloride solution, dried over magnesium sulphate and concentrated. The nitrobenzene was removed by distillation at 80°–100° C. and 20 Pa. By distillation at 240°–250° C. and about 13.4 Pa there were obtained 1.32 g (74%) of 4-chloro-4'-(7-chloroheptyl)-benzophenone as a light yellow oil.

$^1$H—NMR (CDCl$_3$): 1.2–1.9 (m, 9H); 1.72 (t, J=7.5 Hz, 2H); 3.53 (t, J=7.2 Hz, 2H); 7.2–7.9 (m, 8H) ppm.

c) 1.32 g of 4-chloro-4'-(7-chloroheptyl)benzophenone and 0.85 g of sodium iodide were heated under reflux in 20 ml of ethyl methyl ketone. After 24 hours the reaction mixture was evaporated. The residue was suspended in 50 ml of water, whereupon the suspension was extracted three times with 50 ml of ethyl acetate each time, the combined organic phases were washed with 50 ml of a saturated sodium chloride solution, dried over magnesium sulphate and evaporated. There were obtained 1.5 g (90%) of crude 4-chloro-4'-(7-iodoheptyl)benzophenone as a yellowish oil which was used in the next step without further purification.

d) This crude oil was treated with 10 ml of a 33 percent solution of dimethylamine in ethanol, the mixture was stirred at room temperature for 24 hours and then evaporated, the residue was taken up in 50 ml of 1N hydrochloric acid and washed three times with 50 ml of ether each time. The aqueous phase was made basic with 2N sodium hydroxide solution while cooling with ice and extracted three times with 50 ml of ether each time. The organic phases were dried over magnesium sulphate and evaporated. The crude product was chromatographed on 100 g of silica gel with methylene chloride/methanol/ammonium chloride 90:10:1. There were obtained 0.6 g (51%) of 4-chloro-4'-[7-(dimethylamino)heptyl]benzophenone as a colourless oil.

Mass spectrum m/e: 357 (0.6%, M+), 128 (4%), 58 (100%).

EXAMPLE 14

The compounds listed hereinafter were manufactured in analogy to Example 13:

a) 4-Bromo-4'-[7-(dimethylamino)heptyl]benzophenone as a colourless oil (yield 38%). The corresponding hydrochloride with a melting point of 122°–123° C. was obtained by treatment with ethereal hydrochloric acid (yield 85%).

b) 2,4-Dichloro-4'-[7-(dimethylamino)heptyl]benzophenone as a colourless oil (yield 73%).

Mass spectrum m/e: 391 (0.3%, M+), 173 (1.3%), 128 (4.2%), 58 (100%).

c) 4-[4-(Dimethylamino)heptyl]benzoyl]benzonitrile as a colourless oil (yield 68%).

Mass spectrum m/e: 348 (0.6%, M+), 128 (2.7%), 58 (100%).

d) 4-[7-(Allylmethylamino)heptyl]benzophenone (yield 66%) as a colourless oil.

Mass spectrum m/e: 349 (1.7%, M+), 167 (4.3%), 84 (100%).

e) 4-[7-(Allylmethylamino)heptyl]-4'-bromobenzophenone as a light yellow oil (yield 62%).

Mass spectrum m/e: 427 (0.7%, M+), 400 (3.3%), 84 (100%).

f) 4-[4'-[7-(Allylmethylamino)heptyl]benzoyl]benzonitrile as a yellow oil (yield 46%).

Mass spectrum m/e: 374 (2%, M+), 345 (8%), 84 (100%).

g) 4-Bromo-4'-[6-(dimethylamino)hexyl]benzophenone hydrochloride (yield 72%) as colourless crystals with a melting point of 115°-117° C.

h) 4-[6-(Allylmethylamino)hexyl]-4'-bromobenzophenone (yield 77%) as a colourless oil.

Mass spectrum m/e: 415 (0.8%, M+), 413 (0.8%), 386 (2%), 84 (100%).

i) 3-Bromo-4'-[6-(dimethylamino)hexyl]benzophenone (yield 48%) as a light yellow oil.

Mass spectrum m/e: 387 (0.3%, M+), 114 (7%), 58 (100%).

j) 4-[6-(Dimethylamino)hexyl]-2'-methylbenzophenone (yield 36%) as a light yellow oil.

Mass spectrum m/e: 325 (0.9%, M+), 114 (8%), 58 (100%).

k) 4-[6-(Dimethylamino)hexyl]-4'-nitrobenzophenone (yield 80%) as a yellow oil.

Mass spectrum m/e: 354 (0.4%, M+), 114 (6%), 58 (100%).

l) 2-Chloro-4'-[6-(dimethylamino)hexyl]benzophenone (yield 59%). The corresponding hydrochloride with a melting point of 176°-178° C. was obtained by treatment with ethereal hydrochloric acid (yield 86%).

m) 4-[7-(Dimethylamino)heptyl]-2-methylbenzophenone as a colourless oil.

Mass spectrum m/e: 337 (1.5%, M+), 128 (6%), 105 (4%), 77 (3%), 58 (100%).

EXAMPLE A

The compound 4-[7-(dimethylamino)heptyl]benzophenone can be used as follows as the active ingredient for the manufacture of tablets:

| Ingredients | mg/tablet |
| --- | --- |
| Active ingredient | 200 |
| Powd. lactose | 100 |
| Povidone K 30 | 15 |
| Na carboxymethylstarch | 10 |
| Talc | 3 |
| Magnesium stearate | 2 |
| Tablet weight | 330 |

The active ingredient and the powd. lactose are mixed intensively. The mixture obtained is then moistened with an aqueous solution of Povidone K 30 and kneaded, whereupon the mass obtained is granulated, dried and sieved. The granulate is mixed with the remaining ingredients and then pressed to tablets of suitable size.

We claim:

1. A method for treating a mammal having infections caused by pathogenic fungi, which comprises administering to said mammal a compound of the formula

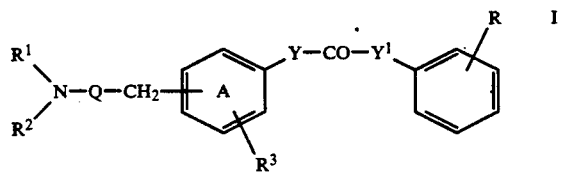

wherein each of $R^1$ and $R^2$ individually is hydrogen, lower alkyl, or lower alkenyl, $R^3$ is hydrogen, halogen or lower alkyl, Q is alkylene with 2 to 11 carbon atoms and at least 2 carbon atoms between the two free valencies or alkenylene with 4 to 11 carbon atoms and at least 4 carbon atoms between the two free valencies and each of Y and Y' individually is a direct bond; the group $R^1R^2N$—Q—$CH_2$— is attached to the 3- or 4-position of ring A and the symbol R designates that the ring to which it is attached is unsubstituted or is substituted with at least one of halogen, trifluoromethyl, cyano, nitro, lower alkyl or lower alkoxy, or a pharmaceutically acceptable acid addition salt thereof in an amount which is effective in treating infections caused by pathogenic fungi.

2. A method of prophylaxis against the development of pathogenic fungi infections which comprises administering to mammals susceptible to such infections a prophylactically effective amount of a compound of the formula I

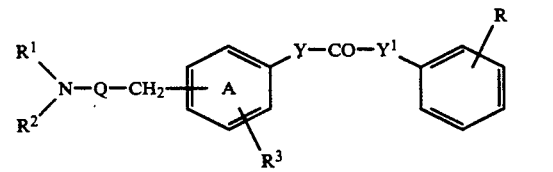

wherein each of $R^1$ and $R^2$ individually is hydrogen, lower alkyl, or lower alkenyl, $R^3$ is hydrogen, halogen or lower alkyl, Q is alkylene with 2 to 11 carbon atoms and at least 2 carbon atoms between the two free valencies or alkenylene with 4 to 11 carbon atoms and at least 4 carbon atoms between the two free valencies and each of Y and Y' individually is a direct bond; the group $R^1R^2$—N—Q—$CH_2$— is attached to the 3- or 4-position of ring A and the symbol R designates that the ring to which it is attached is unsubstituted or is substituted with at least one of halogen, trifluoromethyl, cyano, nitro, lower alkyl or lower alkoxy, or a pharmaceutically acceptable acid addition salt thereof.

3. The method of claim 1 wherein each of $R^1$ and $R^2$ individually is hydrogen or lower alkyl, $R^3$ is hydrogen, Q is alkylene with 2 to 11 carbon atoms and at least 2 carbon atoms between the two free valencies and each of Y and Y' individually is a direct bond; the group $R^1R^2$—N—Q—$CH_2$— is attached to the 3- or 4-position of ring A and the symbol R designates that the ring to which it is attached is unsubstituted or is substituted with at least one of halogen, trifluoromethyl, nitro, lower alkyl or lower alkoxy.

4. The method of claim 2 wherein each of $R^1$ and $R^2$ individually is hydrogen or lower alkyl, $R^3$ is hydrogen, Q is alkylene with 2 to 11 carbon atoms and at least 2 carbon atoms between the two free valencies and each of Y and Y' individually is a direct bond; the group $R^1R^2$—N—Q—$CH_2$— is attached to the 3- or 4-position of ring A and the symbol R designates that the ring to which it is attached is unsubstituted or is substituted with at least one of halogen, trifluoromethyl, nitro, lower alkyl or lower alkoxy.

5. A compound having the formula

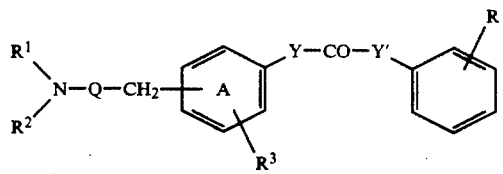

wherein each of $R^1$ and $R^2$ individually is lower alkyl, $R^3$ is hydrogen, Q is alkylene with 6 carbon atoms and at least 2 carbon atoms between the few free valencies, the group $R^1 R^2$—N—Q—$CH_2$— is attached to the 4-position of ring A, each of Y and Y' individually is a direct bond, and R designates that the ring to which it is attached is substituted by at least one of halogen or trifluoromethyl.

6. The compound according to claim 5, 4'-fluoro-4-[7-(dimethylamino)heptyl]benzophenone.

7. The compound according to claim 5, 4-[7-(Dimethylamino)heptyl]-4'-(trifluoromethyl)]benzophenone.

8. The compound according to claim 5, 2,4-difluoro-4'-[7-(dimethylamino)heptyl]benzophenone.

* * * * *